(12) United States Patent
Van de Velde

(10) Patent No.: US 6,789,900 B2
(45) Date of Patent: *Sep. 14, 2004

(54) SCANNING LASER OPHTHALMOSCOPE OPTIMIZED FOR SELECTIVE RETINAL MICROPHOTOCOAGULATION

(75) Inventor: Frans J Van de Velde, Boston, MA (US)

(73) Assignee: Jozef F. Van de Velde, Oosterzele (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/291,958

(22) Filed: Nov. 10, 2002

(65) Prior Publication Data

US 2003/0179344 A1 Sep. 25, 2003

Related U.S. Application Data

(63) Continuation of application No. 09/118,767, filed on Jul. 18, 1998, now Pat. No. 5,892,569, which is a continuation-in-part of application No. 09/075,239, filed on May 9, 1998, now Pat. No. 5,943,117, which is a continuation-in-part of application No. 08/755,448, filed on Nov. 22, 1996, now Pat. No. 5,923,399.

(51) Int. Cl.$^7$ .................................................. A61B 3/10
(52) U.S. Cl. ...................................................... 351/221
(58) Field of Search ................................ 351/200, 205, 351/206, 208, 209, 210, 211, 221, 246; 606/4, 5

(56) References Cited

U.S. PATENT DOCUMENTS 6,179,422 B1 * 1/2001 Lai ............................. 351/210
6,585,722 B1 * 7/2003 Abe ............................... 606/4

\* cited by examiner

Primary Examiner—George Manuel

(57) ABSTRACT

A combination of a confocal scanning laser ophthalmoscope and external laser sources is used for microphotocoagulation purposes. An opto-mechanical linkage device and beam-splitter is used to align the pivot point of the Maxwellian view of the scanning laser ophthalmoscope with the pivot point of non-scanning external laser beams. The same pivot point is necessary to minimize wavefront aberrations and to enable precise focussing of a therapeutic laser beam on the retina. An AOM and/or two-dimensional AOD can be inserted in the pathway of the Gaussian therapeutic beam to control intensity and spatial pattern of small and short-duration pulses. The location of the external laser beam on the retina is determined with the help of two synchronized detectors and image processing. One detector is used to localize moving fiducial landmarks of the retina. A second detector is used to locate on the retina the external laser aiming beam. Two different confocal apertures are used. Polarizing the aiming beam is necessary to further reduce unwanted reflections from the anterior corneal surface.

6 Claims, 7 Drawing Sheets

SCANNING LASER OPHTHALMOSCOPE OPTIMIZED FOR SELECTIVE RETINAL MICROPHOTOCOAGULATION

CROSS REFERENCE TO RELATED APPLICATIONS

This application is a continuation of U.S. patent application Ser. No. 09/118,767, filed Jul. 18, 1998, now U.S. Pat. No. 5,892,569, which is a continuation-in-part of the U.S. patent application Ser. No. 09/075,239, filed May 9, 1998 now U.S. Pat. No. 5,943,117, entitled "Scanning laser ophthalmoscope for retinal microphotocoagulation and measurement of wavefront aberrations, which is also a continuation in part of the U.S. patent application Ser. No. 08/755,448, filed Nov. 22, 1996 now U.S. Pat. No. 5,923,399 and entitled "Scanning laser ophthalmoscope optimized for retinal microphotocoagulation". Both parent applications are herein incorporated by reference. This application is also related to the U.S. Pat. No. 5,568,208, issued Oct. 22, 1996, entitled "modified scanning laser ophthalmoscope for psychophysical applications" and the U.S. patent application Ser. No. 09/033,900, filed Mar. 1, 1998, entitled "Maxwellian view and modulation control options in the scanning laser ophthalmoscope", both referred applications herein incorporated by reference.

BACKGROUND

1. Field of Invention

The invention relates generally to instruments for examining and treating the eye and specifically to a scanning laser ophthalmoscope equipped with external laser sources for the purpose of retinal microphotocoagulation.

2. Description of Prior Art

The ophthalmoscope is well known as an important device for examining the eye, and in particular the retina. As a result of great interest in preserving eyesight, ophthalmoscopes of various constructions have been built. The latest version of the ophthalmoscope, a scanning laser ophthalmoscope, is particularly appealing because of its unique capability of combining infra-red and angiographical imaging of the retina with psychophysical procedures such as the study of visual fixation characteristics, visual acuity measurements, and microperimetry. A precise correlation between retinal anatomy and retinal functioning can be established with the scanning laser ophthalmoscope. This retinal function mapping is now known to be very helpful to the surgeon when applying therapeutic laser. Until now however, these therapeutic laser applications have been delivered to the retina with an instrument other than the scanning laser ophthalmoscope. The use of different instruments renders the comparison of images, the interpretation of psychophysical testing and precision of treatment more difficult.

U.S. Pat. No. 4,213,678, issued Sep. 29, 1980 to Pomerantzeff et al, discloses a co-pupillary scanning laser ophthalmoscope for the purpose of diagnosing and treating retinal disease using two different intensity levels of the scanning laser beam. One intensity range can be used for monochromatic imaging and angiography while a much higher level of the same laser beam or a different coaxial scanning laser beam is used for retinal photocoagulation. This novel approach however is not ideal because of the technical difficulties in implementing safety controls for such a scanning therapeutic laser beam, the difficulty in modulating the scanning laser beam over a range from non-coagulating to coagulating energies at video bandwidths, and the non-thermal complications of high intensity pulsed laser beams in the nanosecond domain with an inappropriate duty cycle. Pulsed thermal microphotocoagulation is however useful to restrict the impact of therapeutic applications to selective layers of the retina, specifically the retinal pigment epithelium. An appropriate duty cycle is necessary. The only solution that is left for effective thermal coagulation, wether pulsed or continuous, is to combine the scanning laser ophthalmoscope with a traditional external non-scanning therapeutic laser source. However, it is impossible to image directly the impact of such therapeutic laser source with a traditional co-pupillary scanning laser ophthalmoscope.

In the prior art, an ophthalmoscope, exemplified by the biomicroscope, is optically combined with a non-scanning therapeutic laser source for the purpose of retinal photocoagulation. In this modality, a contactglass is usually placed on the cornea to be able to view the retina with the instrument, and a mirror is used for reflecting the therapeutic laser beam onto the desired retinal location through a small part of the pupillary area. Importantly, the retina is illuminated and observed through different parts of the pupillary area to avoid reflexes, i.e. Gullstrand's principle of ophthalmoscopy. This optical arrangement makes the art of precise focussing of a small therapeutic laser beam on specific retinal levels, especially a Gaussian beam more difficult in the presence of wavefront aberrations or large diameter entrance beams. More specifically, focussing with a contactglass on the retina is subject to eye and head movements of the patient that easily brings the Gaussian beam out of focus because of its high divergence.

Small therapeutic applications are often desired because they save retinal tissue, also they can be tailored to the shape of the lesion and they can take a variability in absorption more easily into account. However, photocoagulating ophthalmoscopes have been limited when consistent small or localized laser applications in the retina are desired because the anatomical changes caused by the therapeutic laser are difficult if not impossible to visualize during treatment in the presence of photocoagulating light. This is even more the case if minimal intensity, i.e. threshold applications are desired. The critical endpoint of the laser application is often exceeded. The surgeon, upon recognizing the minimal anatomical changes on the retina, is also handicapped by a substantial human reaction time delay before he can interrupt the therapeutic laser. During this delay the laser continues to deliver energy to the retina and changes in the subject's fixation may occur. Since the reaction time of the surgeon may exceed 200 ms, a 100 ms laser application can easily be wrongly targeted on the retina in the case of misalignment.

Also, it is difficult to permanently document previous applications on the retinal image because threshold applications themselves are usually not visible some time after the initial treatment.

OBJECT, SUMMARY AND ADVANTAGES OF THE INVENTION

The principal object of this invention is to combine in one instrument the capabilities of imaging, psychophysics, and microphotocoagulation with optimal focussing and documenting of variable size therapeutic laser applications that are used in threshold and pulsed selective microphotocoagulation. This principal object is accomplished by selecting an entrance location of a spatially and temporally modulated external therapeutic laser beam that is subject to minimal wavefront aberrations through observation of the retina with the scanning laser ophthalmoscope using the same entrance location for the scanning lasers. As documented in the prior art, Gullstrand's principle is used differently in scanning laser ophthalmoscopy, hence the possibility and necessity to use a similar optical pathway for both the therapeutic and scanning laser beams. To implement this solution, several principles have to be taken into account:

(1) A special coupling system between a confocal scanning laser ophthalmoscope and external laser sources is used. It comprises an optimized beamsplitter and dedicated opto-mechanical linkage device. This linkage device allows the alignment of the pivot point for the fast scanning diagnostic laser beams of the scanning laser ophthalmoscope with the pivot point of the non-scanning external therapeutic laser beams. Optimizing the Maxwellian viewing of a retinal location will then also result in a minimal wavefront aberration for the external laser beams because the same pivot point is used. Also in this situation, the amount of prefocussing necessary to image on a specific retinal layer is a reference, if needed, for focussing the therapeutic laser beam with its proper telescopic optics. This telescopic optics can also take into account minimal chromatic aberrations caused by differences in the wavelengths used. The main focusing mirror of the SLO can be incorporated into the opto-mechanical device to simplify the mechanical angulating mechanism of the external therapeutic laser beam.

(2) As mentioned before, a non-confocal or co-pupillary scanning laser ophthalmoscope cannot be used to detect the impact of the external laser beam on the retina. The confocal instrument can do this, however under specific conditions only. It is important to realize that the reflection image of the therapeutic application on the monitor is actually a convolution of the actual external laser spot with the confocal aperture. Usually the confocal aperture of the scanning laser ophthalmoscope is larger and hence the backscatter image cannot be used directly to determine size or adjust focussing. The foregoing necessitates either indirect focussing as mentioned before by using the same pivot point and relying on the focussing of the retinal image, or preferably the use of a specially constructed double aperture with different size pinholes.

(3) Although it is possible to realize part of the invention with one detector pathway, considerable advantages are derived from using two detectors that are temporally synchronized in the confocal scanning laser ophthalmoscope. Reasons are the weak contrast of the aiming beam on the retinal image, obscuring therapeutic light, and the fact that the retina and therapeutic laser spot can move independently of each other. Using an appropriate beamsplitter and filters, one detector images the retina, its pigment distribution and the anatomical changes caused by the therapeutic laser, unimpeded by the therapeutic laser light. Reference fiducial landmarks in the retinal image can be retrieved with two-dimensional normalized grayscale correlation faster than human reaction time would allow. A second synchronized detector images only the backscattered light from the external laser beams, without a background of moving retinal details. This image can be localized using simple image processing techniques such as look-up table manipulation. The implementation of a two detector pathway therefore allows registration of therapeutic laser applications, referenced on the retinal image, and the use of a safety shutter in case of excessive misaligment. It should be noted that this specific part of the invention could equally be applied to traditional photocoagulating systems if they are equipped with two video cameras, as long as the detector images are made spatially congruent.

(4) An aiming beam of different wavelength than the actual therapeutic laser source is polarized, and is transmitted after backscattering from the retina through the polarizing beamsplitter. Only the aiming beam wavelength, properly polarized, is allowed to reach a photodetector in order to avoid strong corneal reflections that may seem as a second spot on the retinal image.

(5) If the therapeutic laser beam is Gaussian in nature, it can easily be modified with the help of an acousto-optic modulator or two-dimensional acousto-optic deflector. This will create a pattern of microphotocoagulation spots of various duration and intensity that are easy to focus without a contactglass onto the retina with the SLO. Head movements of the patients become far less important as a near collimated and wide entrance beam is used on the cornea for which a large depth of focus or Raleigh zone exists. This cannot be accomplished with an ordinary slitlamp and eye contactglass. This is the major advantage of the current invention and continuation.

The invention allows to accurately place and document small, minimal intensity therapeutic laser applications to selected layers of the retina, hence the term microphotocoagulation or selective photocoagulation. With the proper selection of wavelength and therapeutic laser duration and pulse characteristics, selective targeting of retinal pigment epithelium layer and a various amount of sensory retina can be accomplished. Immediate microperimetric and angiographic feedback is available.

Microphotocoagulation has the ability to remove temporarily or permanently a percentage of the metabolically very active photoreceptors and retinal pigment epithelium cells, while minimizing damage to other anatomical structures, especially the nourishing choriocapillary layer, delicate Bruch's membrane, ganglion cell layer and neural tissue in between applications. Virtual "oxygen windows", reducing relative hypoxia, can for example be established through reduction of the demanding metabolic load of the central retina. This approach is useful in the retardation of onset or prevention of drusen related and neovascular age-related maculopathy. Possible mechanisms are an accelerated removal of material that thickens Bruch's membrane and the reduced production of angiogenetic factors caused by relative hypoxia. Debridement of retinal pigment epithelial cells may lead to the removal of infectious agents, accumulated intracellular material or replacement of otherwise defective retinal pigment cells. The retinal location, focussing, size, intensity and duration of often invisible therapeutic laser applications can be stored and used for follow-up evaluation.

Further objects and advantages of the invention will become apparent from a consideration of the drawings and ensuing description of a preferred embodiment.

DESCRIPTION OF THE DRAWINGS

In FIG. 3a, a common pivot point is used to avoid lens changes in this example, thereby resulting in minimal wavefront aberrations and calculable focussing of the therapeutic beam location in the retina. In FIG. 3b, spurious reflections are possible at the anterior corneal interface and are dealt with differently for scanning and therapeutic beams. If the two-dimensional AOD creates a pattern, the external laser will use a pivot point that is only deviating minimally from the ideal common pivot point.

FIG. 9a shows the two dimensional pattern of focussed Gaussian beam spots, the pattern itself is variable, typically containing 5 to 10 spots on a side of 20 mu diameter. FIG. 9b illustrates the general ray-tracing with a practically collimated and wide beam entering the eye optics. Acousto-optic deflection only causes minimal deviation from the axial reference beam that shares the pivot point with the SLO scanning laser beam (up to 10 minutes of arc only). Importantly, if the eye optics move back and forth, the focusing of the spots will be minimally affected. This would not be the case if the eye optics were neutralized with a flat contactglass as in the case of slitlamp delivery. FIG. 9c illustrates one of several possible duty cycles for selective coagulation. About 5 to 10 mu J are delivered per pulse, pulse duration of 5 mu s and interval between same spot exposure of about 2 ms.

REFERENCE NUMERALS IN DRAWINGS

Figure 1:
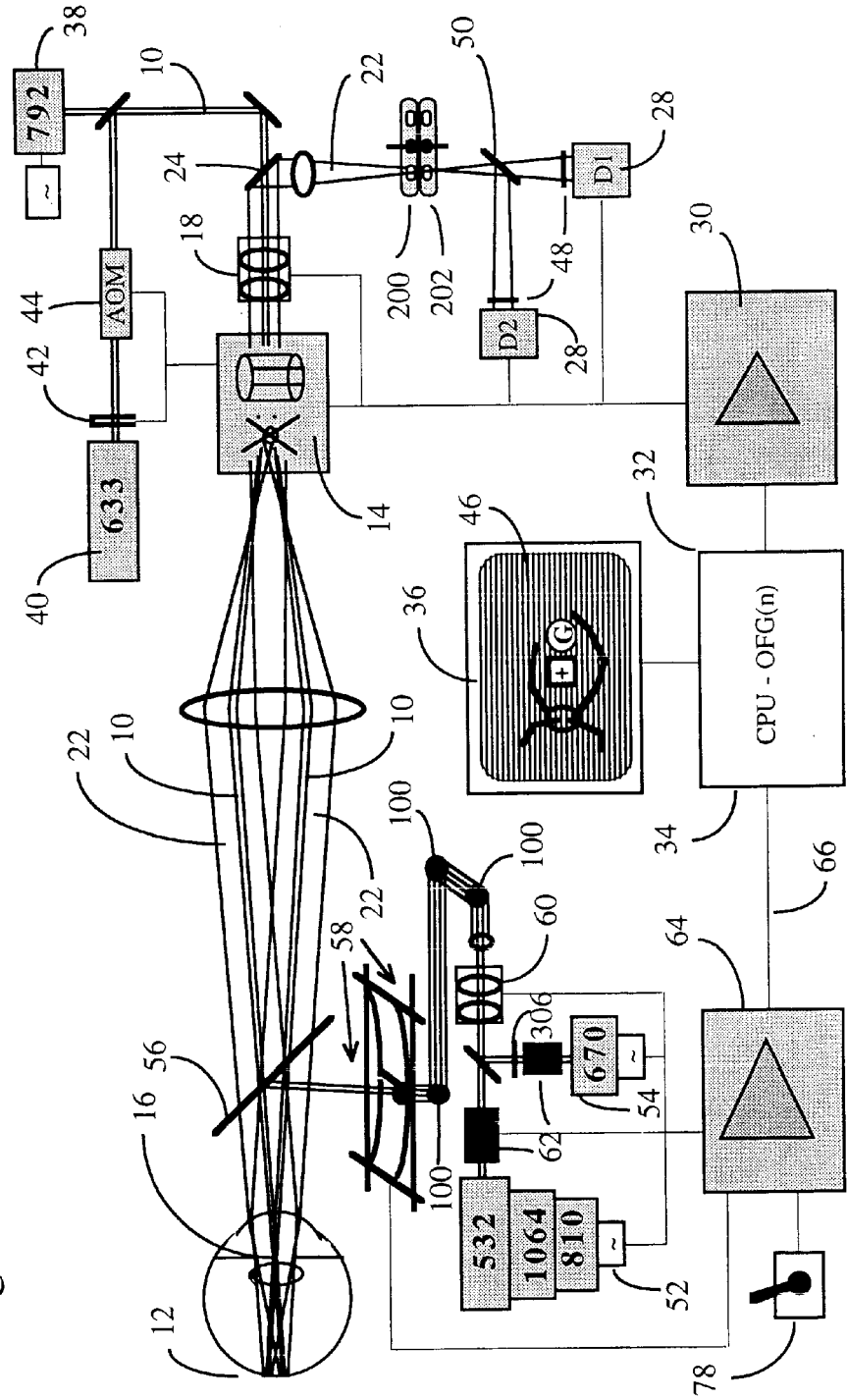
FIG. 1 is a diagrammatic representation, illustrating the different components of the confocal scanning laser ophthalmoscope optimized for microphotocoagulation. Three subparts can be distinguished. (1) A confocal scanning laser ophthalmoscope with lasers having visible and infra-red wavelengths, synchronized detectors, beamsplitter, confocal apertures with different kind of filters, collimator-telescope prefocussing optics, scanning optics, sync and video-generating electronics, acousto-optic (AOM) or direct electrical amplitude modulation (EAM) of lasers. (2) External therapeutic non-scanning lasers with modulation options including AOM and two dimensional AOD, coupled to the scanning laser ophthalmoscope with the help of a beamsplitter and opto-mechanical linkage device, safety shutter, collimator-telescope, and interface electronics. (3) The computer with one or more linked overlay frame grabber graphic cards, capable of digital image processing, and monitor.

10 Gaussian beams of laser light of scanning laser ophthalmoscope, coaxial
12 Posterior pole of the eye, retina
14 Scanning optics, including polygon and galvanometer, additional lenses, mirrors
16 Similar Maxwellian view of scanning and therapeutic beams, common pivot point
18 Collimator-telescope for scanning laser beams of ophthalmoscope
20 Lens changes, scattering elements in the optical media of the eye
22 Backscattered light returning from the retina
24 Beamsplitter or aperture for separation of incident and backscattered laser light
26 Combining beamsplitter (polarizing)
28 Avalanche photodiode detectors
30 Video and sync generating electronics of scanning laser ophthalmoscope
32 Computer
34 Overlay frame grabber graphic cards
36 Video display monitor
38 SLO diode infra-red 792 nm laser for imaging purposes
40 SLO He—Ne 633 nm laser for microperimetric purposes
42 Pair of adjustable linear polarizers, attenuators
44 Acousto-optic modulator
46 Overlay graphics on retinal image, indicating characteristics of external laser spot
48 Barrier, interference or polarizing filters, optionally with pinhole in 200 or 202
50 Beamsplitter for separating scanning (imaging) and external (aiming) laser beams
52 External, non-scanning therapeutic laser, e.g. frequency doubled diode pumped YAG
54 Second wavelength external laser source, e.g. diode 635 nm or 670 nm
56 Beamsplitter combining light from scanning and external laser sources
58 Opto-mechanical linkage device
60 Collimator-telescope for external laser beams
62 Safety shutter, acousto-optic modulator, mechanical chopper, or two-dimensional acousto-optic deflector
64 Electronic circuitry for elements 52, 54, 58, 60, 62
66 I/O link between supporting electronics 64 and computer
78 Joystick-micromanipulator
90 Reflected light at the anterior corneal interface
100 Adjustable mirror hinges, interconnected with ball-bearing adjustable cylinders
102 Support arc for positioning distal element 100

104 Pair of support arcs for positioning element 102
106 Supporting framework for elements 100, 102 and 104
108 Adjustable lead screw support for positioning element 106
110 Framework with adjustable lead screw to position element 108
112 Stepping motors, screws or mechanics to position the elements 100, 104, 106, 108
114 Fixed attachment to the scanning laser ophthalmoscope of element 58
116 Ball-bearing cylinders with rotational and translational capabilities
118 One half of clamp around torical support arc
120 Torical support arc, completely closed
150 Dioptric media of the eye, eye optics
152 Cornea
154 Lens of the human eye
156 Anterior chamber fluid
158 Vitreum
160 Retina in toto
162 Photoreceptor layer
164 Nerve fiber layer with internal limiting membrane
166 Choriocapillary layer
168 Retinal pigment epithelium layer
170 Bruch's membrane layer
172 A virtual conjugate image of apertures 200 and 202, if adjusted to coincide
174 Scattering from non-scanning external laser source at the retina
176 Ray tracing of stationary scanning laser (Gaussian) through optic media
200 Wheel containing different apertures for external laser sources
202 Wheel containing different confocal apertures for scanning laser sources
204 Small opening, tightly confocal thin aperture, but transparent for scanning lasers
206 Larger opening, less confocal aperture for scanning laser sources
208 Similar to 204
210 Larger confocal opening when compared with 206
250 Pixels representing high intensity interval of modulated Gaussian therapeutic laser
260 Videolines representing interval between therapeutic laser pulses
270 Additional high intensity pixels to counter aliasing of aiming beam
300 Fiber carrying 532 nm laser light from source 52
302 Aperture of 75 to 100.mu., numerical aperture N.A. 0.05-0.08
304 Combining beamsplitter
306 Polarizer
308 Acousto-optic modulator
310 670 diode laser source, aiming beam 54
312 Relay optics, inclusive element 60 and optional field lenses
314 Receiving optics, eye with f, 22.28 mm and having f/10, 2 mm entrance pupil
316 Fiber optic similar to 300

DETAILED DESCRIPTION AND OPERATION OF AN EMBODIMENT

A typical embodiment of the confocal scanning laser ophthalmoscope for retinal microphotocoagulation is illustrated in FIG. 1. The principles of scanning laser ophthalmoscopy are described in detail in the prior art (Pomerantzeff, Saban, Webb, Plesch). Features of the confocal scanning laser ophthalmoscope that are relevant to the invention are further discussed.

I. The Confocal Scanning Laser Retinoscope

A prefocussed Gaussian beam of laser light 10, e.g. consisting of a merger of polarized He—Ne 633 nm and diode 792 nm, and having an approximate diameter of 1.0 mm at the entrance of the eye, is further focussed by the eye optics of approximately 60 D power, to a spot, typically between 10 and 30.mu. in diameter at a retinal plane, and this spot is scanned over the posterior pole of the eye 12 in a sawtooth manner with the help of scanning optics, currently comprising a polygon and galvanometer driven mirror 14. Fast horizontal 15 KHz and slower vertical 60 Hz deflections of this flying laser spot correspond to a standard video RS-170 rate and create the rectangular laser beam raster on the retina. A rectangular area of about 0.5 cm.sup.2 on the retina is illuminated in the 40 degree field of view of the instrument. A Maxwellian view illumination is used in the scanning laser ophthalmoscope. The pivot point 16 of the scanning laser beam is well-defined and is optimally positioned, e.g. in the plane of the anatomical pupil, in order to minimize the effect of wavefront aberrations on the retinal image. The amount of prefocussing is adjusted with a collimator-telescope 18 that is used to position the waist of the Gaussian beam at specific planes in the retina. The field of view can be changed from 40 degrees to 20 degrees with the help of additional mirrors. In the 20 degree field of view, the pivot point 16 of the Maxwellian view is wider in diameter as the Gaussian beam diameter is doubled. Because of the wider beam in the 20 degree field of view, it will already be more difficult to minimize wavefront aberrations by moving the pivot point around focal scattering or absorbing elements in the ocular media 20, also the focussing range will be reduced four-fold in accordance with Gaussian beam optics.

In the confocal scanning laser ophthalmoscope, the light that is backscattered and reflected from the retina 22, now distributed in the anatomical pupil, is descanned over the same optics and separated from the illuminating beam at a mirror-pinhole 24. This mirror-pinhole 24 is optimally positioned with regard to light collection, e.g close to a pupillary conjugate plane, and the pinhole also blocks the perpendicularly and specularly reflected light coming from the anterior surface of the cornea along the same path that was used for illumination. Other options are available and have been used before. For example, a polarizing beamsplitter can be applied in combination with a polarizing filter. This would allow the use of axially backscattered light from the retina with some advantages, but puts other optical constraints, especially with regard to polarization and intensity, on the illuminating sources. The returning light is focussed to pass through a small aperture 200, 202. This aperture, e.g. 1 mm in diameter, is conjugate with a virtual aperture 172 of e.g. 100.mu. at the retinal beam waist. Therefore, it moves along with the illuminating beam of the SLO. It is used to reduce the multiple backscattered light outside the illuminated area on the retina. As a result, contrast of the image is considerably enhanced. A smaller aperture would reduce the amount of light returning to the detectors and render the images very confocal to the point of being tomographical in nature. Not to cut back to much on the returning light, especially in the presence of a pinhole 24, the aperture is sometimes up to three times larger than the actual retinal spot being illuminated. The amount of light that falls on an avalanche photodetector 28 after passing appropriate filters, is translated into an analog signal by the video and synchronization generating circuitry 30 of the scanning laser ophthalmoscope. This signal is synchronized to the master timing provided by the rotating polygon. The video signal is then relayed to the overlay frame grabber graphics cards 32 within the computer 34, which in turn will display the processed signal onto a display monitor 36 with appropriate overlays 46.

Often two laser sources are combined to illuminate the retina. The two lasers serve a different purpose. For example, a high intensity diode infra-red 792 nm laser 39, under electrical modulation control and vertically polarized, is nearly invisible to the observer. It produces the retinal image on the display monitor 36. An aligned and low intensity He—Ne 632.8 nm laser 40, horizontally polarized, is modulated with a pair of linear polarizers 42 and acousto-optic modulator 44. The 633 nm laser 40 is used to draw visible graphics in the laser raster. These visible graphics are created by amplitude modulation of the laser 40. For this purpose, the acousto-optic modulator 44 is usually driven by the same computer overlay frame grabber graphics card 32. The graphics, which are seen by the observer, are usually not visible in the retinal image, unless when they are very bright. The exact position and characteristics of the graphics can however be indicated in real-time on the retinal image with the help of computer generated overlays 46 because the image video that comes out of the scanning laser ophthalmoscope and graphics video that modulates the acousto-optic modulator 44 are synchronized to the same timing signals provided by the synchronization generating circuitry 30. The 632 nm He—Ne laser 40, typically used for generating the graphical stimuli at lower intensities, could however also be used for imaging at higher intensity levels.

Multiple and synchronized detectors 28 and multiple laser sources 38,40 have been used before in the original red-yellow krypton color co-pupillary scanning laser ophthalmoscope. Appropriate barrier filters, interference filters 48, and separating beamsplitter 50 are necessary in this situation, matching the different wavelengths that are used. Barrier filter properties can also be combined with apertures 200, 202. Some field lenses and additional optical elements to switch between the 20 and 40 degree field of view have been omitted from the schematic.

Surface-emitting quantum-well laser diodes are of increasing interest, and offer the advantages of high packing densities on a wafer scale. An array of tiny individually modulated cylindrical $In_{0.2}Ga_{0.8}As$ surface-emitting quantum-well laser diodes, VCLES, with lasing wavelengths in the vicinity of 970 nm and shorter can substitute the traditional laser sources 38, 40 and scanners 14 if coupled with a two-dimensional detection array. The use of such a specific extended detection array has been discussed in the original U.S. Pat. No. 4,213,678.

Different External Laser Sources and Their Controlling Means

External therapeutic laser sources 52, 54 are well known in the prior art, e.g. argon or currently diode laser 52, having the possibility of emitting different wavelengths, for example 488 nm, 514 nm, 532 nm, 810 nm and 1064 nm. A variable part of the optical transmission usually occurs in fiber optics. The advantage of fiber optics is flexibility and a more even intensity profile at the exit aperture of a multimode fiber. Multimode propagation of higher intensity laser beams and fiber optics transmission are more difficult to focus to a small spot size when compared with a fundamental mode Gaussian beam due to the $M^2$-factor of propagation or limitations in N.A. of the optical fiber. A pure Gaussian profile would be used for the purpose of measuring wavefront aberrations of the eye or for adjusting the intensity and position of the beam on the retina, thus creating a spot with different spatial and temporal characteristics.

The Gaussian beam of external therapeutic lasers can be pulsed, for example with the help of an acousto-optic modulator 62 or Pockel cell. Either first diffracted or undiffracted zero order beam can be used. If different wavelengths pass through the AOM, achromatizing prisms can be used. It is also possible to use an attenuated and zero order as aiming beam, after optical recombination with the modulated first order beam. It is nevertheless difficult to modulate a multimode laser beam of 50 mrad divergence. A large Bragg angle and therefore high frequency carrier signal e.g. of 1 Ghz would be necessary. A Gaussian 300 mW output at 532 nm (Crystalaser, Irvine Calif.) is easy to modulate with the AOM. The light can be then fed into an optical fiber for mode scrambling. A mechanical light chopper 62, can also be inserted in the optical path of the therapeutic laser beam. An example is a circular disc of 150 mm diameter pierced with 0.5 mm holes at the outer edge. A motor with rotational speed up to 5000 RPM can be used. Several pulse characteristics can be created on adjacent trajectories. The wheel can then be moved to select one of them. Direct electrical modulation using video for the aiming beam diode laser and diode pumped doubled frequency laser 52 or Q-switching of a continuously pumped Nd-YAG laser are other options. The modulation characteristics are further discussed. This pulsing is done to selectively target absorbing layers, for example the pigment epithelium 168.

Alternatively, a two-dimensional acousto-optic deflector can be used. For example, the DTD-274 from Intra-Action Corp. The modulator is controlled by a two channel variable frequency source. A Gaussian therapeutic beam, for example a 500 mW CW 532 nm from Laser Quantum can be deflected in two dimensions according to the voltages applied by the controlling electronics. The AOD can for example create a grid of 10 by 10 spots, each spot about 20 mu in diameter (diffraction limited). Because of this scanning, the total area that is treated will have a diameter of 200 mu, but the Gaussian beam will only dwell for about 5 micro seconds on a single spot. Because of the small diameter of each individual spot, a low powered external laser source is sufficient. It is easily possible to obtain about 6 micro J/pulse during 5 microsec. With the same small spot being retreated after an interval of 2000 micros; during this interval the other adjacent spots are being illuminated by the AOD deflection pattern. In such manner, selective coagulation of the RPE can be obtained in a reasonably sized spot with a low power laser source. Several other patterns of duration and size can be programmed with the two channel variable frequency source, raster wise continuous or discontinuous. This delivery method is quite different from the traditional way of delivering the pulsed application, where the size that is irradiated is large and the laser output is chopped, losing the laserpower in between applications on the same area. A potential disadvantage of the AOD delivery method is the fact that focusing is critical because of the high divergence of the beam. Indeed, with a larger application size it would not. As mentioned before, because of the focusing issue, the SLO is the best way of delivering such small spots. There are two main reasons: (1) the Gaussian external therapeutic beam is aligned with the Gaussian imaging beam of the SLO. If the image is in focus, the therapeutic beam will also be in focus. It should be noted that because of the AOD scanning, the actual treatment spot will only be perfectly aligned centrally, but since the treatment area is small, there will only be a small angle of deviation with the axis of the imaging beam, esssentially still using the same entrance location at the pupil. (2) As mentioned before, the near collimated delivery of the beam at the cornea, without contactglass, allows for some natural back and forth movement of the head of the patient. This is impossible with the slitlamp delivery method described before, where any movement of the head will quickly bring the waist of the Gaussian beam out of focus.

Therapeutic lasers can be used in association with absorbing dyes. In photodynamic therapy, a photosensitizing drug is first injected and laser is then applied with the aim of closing off small blood vessels. In a second stage, classic 514 or 532 nm photocoagulation can penetrate more completely in deeper layers because the blood flow has been halted before with this photodynamic therapy and stationary hemoglobins are far more effective in absorbing energy, together with the melanin pigment. Another dye, e.g. fluorescein, can be injected between the photoreceptors 162 and pigment epithelium 168, thereby causing localized small artificial serous retinal detachments. Delivery of short duration 488 nm applications can then selectively destroy photoreceptors 162 at the dye-photoreceptor interface without destruction of the deeper or more superficial layers 164, 168, 170, 166. Photodynamic therapy is performed with continuous output lasers. In theory, it is possible to use the pulsed microperimetric stimulus of the SLO for this purpose at the right wavelength and proper intensity level because chemical, rather then thermal mechanisms are responsible for its action on the target tissue.

A wide entrance pupil 1064 nm source 52 could at least in theory also selectively coagulate layers in the retina with proper focussing. The main absorbant element will be water as 50% of the incident 1064 nm light will reach the retina. Water is ubiquitous, hence the difficulty in avoiding the inner retina or deeper layers.

Often, an aligned low power therapeutic beam 54 of different wavelength, typically a diode laser in the 630-670 nm range, is provided for aiming purposes. It can be merged at different places with the high power beam 52, pulsed, and it can also be polarized, as energy reduction is of less concern for the aiming beam. Its use has significance in eliminating spurious reflexes from the cornea as further explained. Alternatively, the high power therapeutic laser beam 52 could also serve as an aiming beam at much lower intensities, but would be required to continuously emit power.

Other elements in the optical construction of the therapeutic laser include a safety shutter, stop apertures at the end of the fiber optic, various filters and the modulating devices 62 allowing specific pulsating patterns of energy, typically in the .mu.s domain. The foregoing components are controlled by electronic circuitry 64, known in the prior art. In addition, an I/O link 66, often a combination of TTL circuits, exists between the control electronic circuitry 64 of the external lasers and the computer 34. This electronic connection 66 can signal to the computer 34 when the external lasers 52 and 54 are used and also allows activating the modulating means 62 under control of the computer 34.

As an example we will further elaborate specifically on the 532 nm frequency CW doubled Nd-YAG laser from Iris Medical Corporation, Irvine, Calif. In the current embodiment, an external 670 nm diode is used as aiming laser 54. This diode can be electrically or AOM modulated using computer 32 and anti-aliased with each update of the retinal image. Higher peak powers can then be safely used if necessary.

III. Opto-Mechanical Linkage of SLO and Therapeutic Lasers

Figure 2:
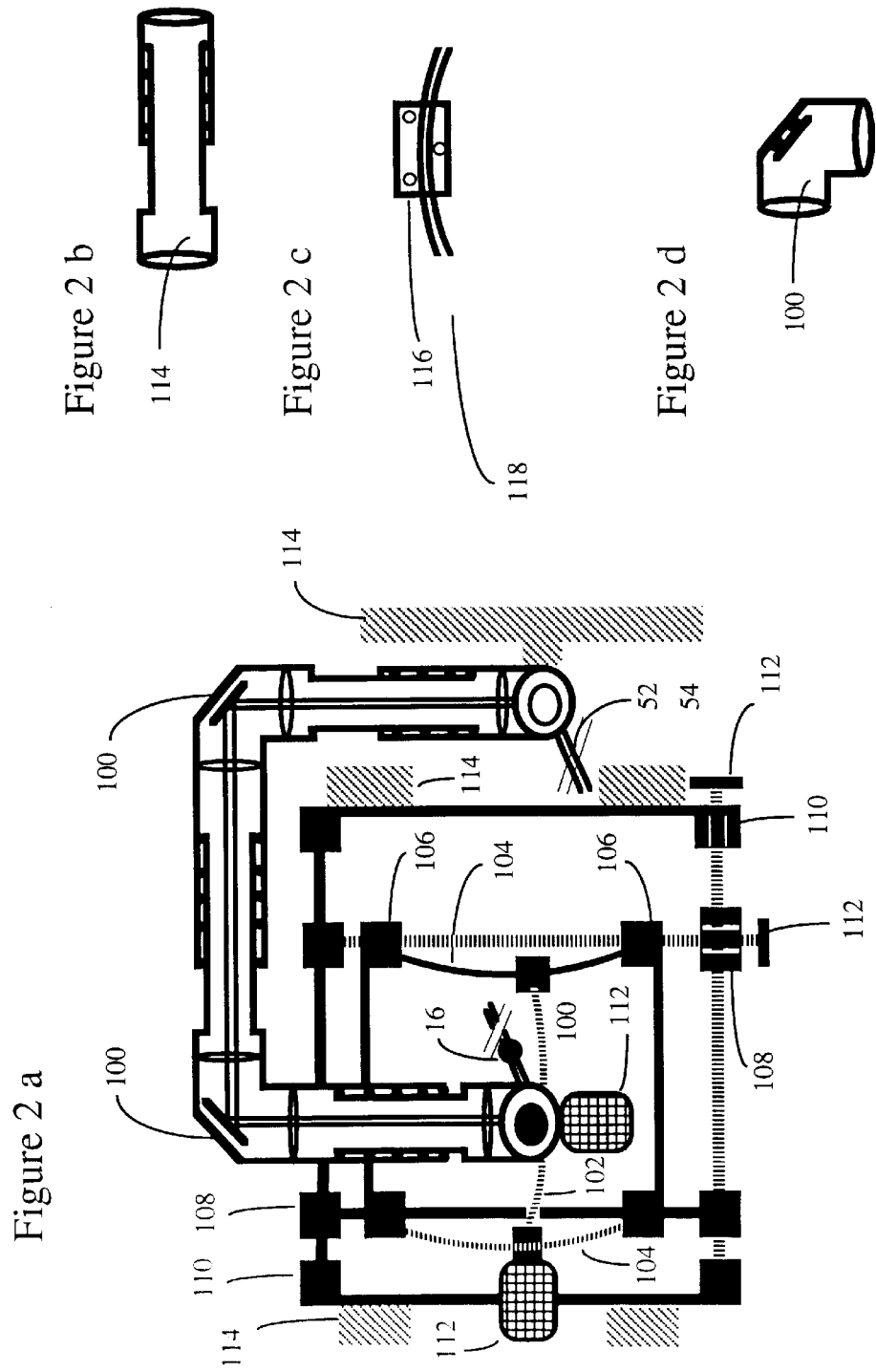
FIG. 2 details the opto-mechanical linkage device coupling external laser sources and confocal scanning laser ophthalmoscope. Angulation of the laser beam is possible mechanically or with the help of stepping motors under CPU control. The pivot points of external lasers and scanning lasers can be adjusted relative to each other. overview image and different essential components are illustrated. By incorporating the main mirror of the SLO in the pathway of the external laser, angulation of the external laser beam can be simplified.

The external therapeutic laser beams 52, 54 are non-scanning, or scanning over a minimal excursion at a specific rate with the help of the two-dimensional acousto-optic modulator, however their general orientations are allowed to change using a special transmission system comprising an appropriately coated beamsplitter 56 and opto-mechanical linkage device 58. FIG. 2 illustrates the essential components of the opto-mechanical linkage device 58 between the external therapeutic laser sources 52, 54 and the confocal scanning laser ophthalmoscope for the purpose of microphotocoagulation. Also, the methods are described by which (1) the position and characteristics of the external laser beams 52, 54 are referenced on the retinal image, (2) a precise focussing is obtained for the purpose of microphotocoagulation, and (3) wavefront aberrations influencing the shape of the therapeutic laser beams are minimized. Also (4) the optical constraints are discussed with regard to optical throughput, as are (5) the characteristics of the different possible barrier, bandpass, interference and polarizing beamsplitters. (6) Also a mechanism is necessary to reduce the specular reflections from the anterior surface of the cornea.

A part of the opto-mechanical linkage device 59 that transmits the therapeutic laser beams is often realized with a combination of extendable mirror hinges 100. Enough degrees of freedom are available with the mirror hinges 100 as to permit unimpeded movement of the laser beams in a rotational and translational fashion. The hinges themselves are connected with ball bearing elements 114 for smooth rotation and extension.

The opto-mechanical linkage device 58 consist further of a framework or base 106 that permits a support arc 102 to slide across using another pair of support arcs 104. The support arcs are part of a toroid 118 and can contain a groof or thread. The last mirror hinge 100 can contain additional optical elements and is attached to the support arc 102. The proximal or first mirror hinge 100 is fixed to the SLO. The terminal part of the transmission optics can slide along the support arc 102 with the help of an attachment 116 and reflects the therapeutic laser light 52, 54 coming from the other components in the opto-mechanical linkage device 58 towards the posterior pole of the eye 12. The two sliding movements allow the external laser beams 52, 54 to move perpendicular to a curved surface, e.g. a part of a sphere, such that the external laser beams 52, 54 will have a pivot point 16 that is very similar in location to the pivot point of the Maxwellian view of the scanning laser ophthalmoscope. The two sliding movements can be produced with the help of stepper motors 112, but several other means and methods can be easily envisaged to perform this function, either manually or motorized. A micromanipulator-joystick 78 is used to control these stepper motors or mechanical movements. The joystick 78 is moved by the surgeon to select a retinal location to treat. The supporting framework 106 typically measures about 100 mm by 100 mm and is attached to the confocal scanning laser ophthalmoscope through the adjustable supporting elements with optional lead screws 108 and 110. The elements 108 and 110 permit the framework 106 to move translationally in two directions. They allow calibration so that the two pivot points coincide. The whole mechanism can be considered a variation of a gimbaled contrivion where the pivot point does not necessarily coincides with the intersection of the two axes of the gimbal.

An alternative delivery system incorporates the main mirror or lens of the SLO. At this point, the mechanical part is reduced to a simpler angulating mirror in two dimensions. However, additional lenses are needed to bring the external laser beams back into focus.

The prefocussed external laser beam 52 usually has a 0.5 mm to 2 mm diameter at the entrance position in the eye, depending on the desired spot size on the retina, the diameter of the fiber optic and its numerical aperture. The external beams 52, 54 are prefocussed by a collimator-telescope 60 using as a reference the amount of prefocussing of the scanning laser beams 38, 40 for the same retinal location and using the same pivot point 16.

Essential in the optical pathway is a collimator-telescope 60 and optional field lenses for precisely selecting the spot size and focussing of the external laser beams 52, 54 on a specific retinal plane. The amount of focussing that is needed for the external laser beams 52 and 54, is related to the amount of prefocussing of the scanning lasers 38 and 40 for the same retinal area since the same optical pathway is used through the ocular media. This focussing can further take into account the dispersion of light that is caused by differences in wavelength. Longitudional chromatic aberration is more important than lateral chromatic aberration since the pivot point is closely located to the nodal points. The longitudinal differences have been tabulated before and amount e.g. to approximately 0.75 D for 532 nm and 792 nm, approximately 0.5 D for the difference between 670 nm and 792 nm. It is possible to use biometric data derived from the keratometer and biometric ultrasound to further refine the ray tracing in the eye. A real time computer algorithm can actually plot, using the foregoing data, on the computer screen the approximate ray tracing inside the eye. This is useful since the surgeon will then be able to confirm that the minimal waist or focus of the beam is situated anteriorly or posteriorly of the retina. The collimator-telescope 60 can be manually or automatically adjusted according to the read-out of the SLO and this can be done on a continuous basis or with fixed interval settings.

If the radius of the gimbaled part of the optomechanical linkage device 58 can be made large enough, the focussing elements can be built into the last element 100 and directly coupled to the end of the fiber optic. This simplifies the construction since no additional extendable mirror hinges are necessary in this case.

Figure 3:
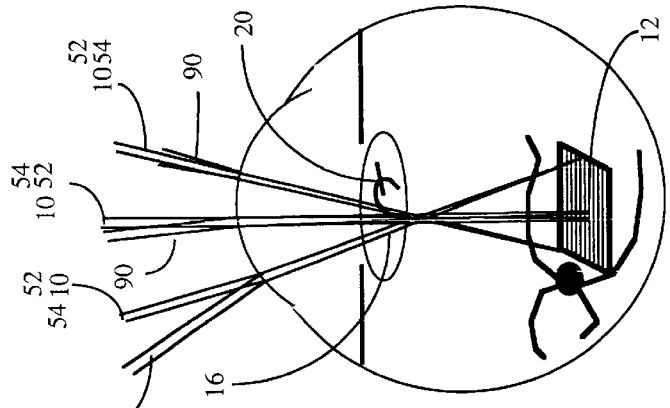
FIG. 3 details the ray tracing of the scanning laser ophthalmoscope and external therapeutic laser beams.
Figure 3:
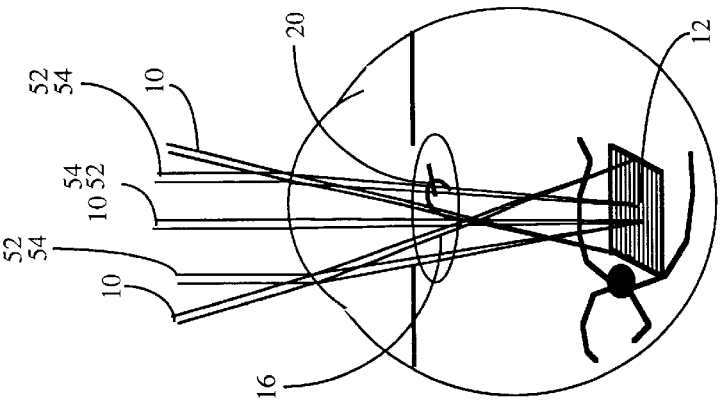

It is important to understand the ray tracing of scanning and external therapeutic laser beams for the purpose of minimizing specular reflections from the anterior surface of the cornea and of wavefront aberrations in the optical media. An optional contact lens positioned on the anterior surface of the cornea can be useful to reduce wavefront aberrations of the anterior surface, may be aspheric, is coated, and can help to keep the eyelids open. It is similar in construction to the Goldmann one-mirror contactglass, except for its curvature. FIG. 3a illustrates the different possibilities that can exist in an eye having some lens changes or scattering elements 20 in the dioptric media that cause wavefront aberrations. Such changes however can occur at the cornea or in the vitreous as well. In order to ensure that both the scanning lasers 38, 40 and external lasers 52, 54 are subject to similar wavefront aberrations, it is necessary that these beams use the same path and hence the same pivot point 16. This pivot point 16 can be chosen by the observer so that a particular retinal location is seen in good focus with minimal aberrations on the monitor 36. As a result, the therapeutic external laser beams 52, 54 will also undergo minimal aberrations and will be easily focussable using the telescope-collimator 60. Also vignetting is avoided and smaller entrance pupils can be used when compared with slitlamp based coagulators. If the pivot points 16 were different, aberrations could influence both the beamshaping and focussing of the therapeutic laser spot. This phenomenon could be exploited to reconstruct the wavefront aberrations of the eye. In the presence of aberrations, a diagnostic external laser spot on the retina will be different by a various amount in quality and more important in location, for the different parallel entrance positions into the eye optics. Different retinal locations are illustrated in FIG. 3a. These differences in location relative to a reference spot created by a fixation target in the scanning laser ophthalmoscope, can be recorded by the frame grabber and subsequently analyzed. Alternatively, the subject could slightly alter the orientation of the external diagnostic beam 52, 54 or fixation target as to neutralize the difference in location on the retina. The amount of angulation required is again a measure of the degree of wavefront aberration corresponding to a particular entrance position of the external beam into the eye optics. The data coming from a grid of different entrance positions could be used to reconstruct the wavefront aberrations across the anatomical pupil of the eye using e.g. the well-known method of Zernike polynomial analysis or equivalent algorithms.

Figure 8:
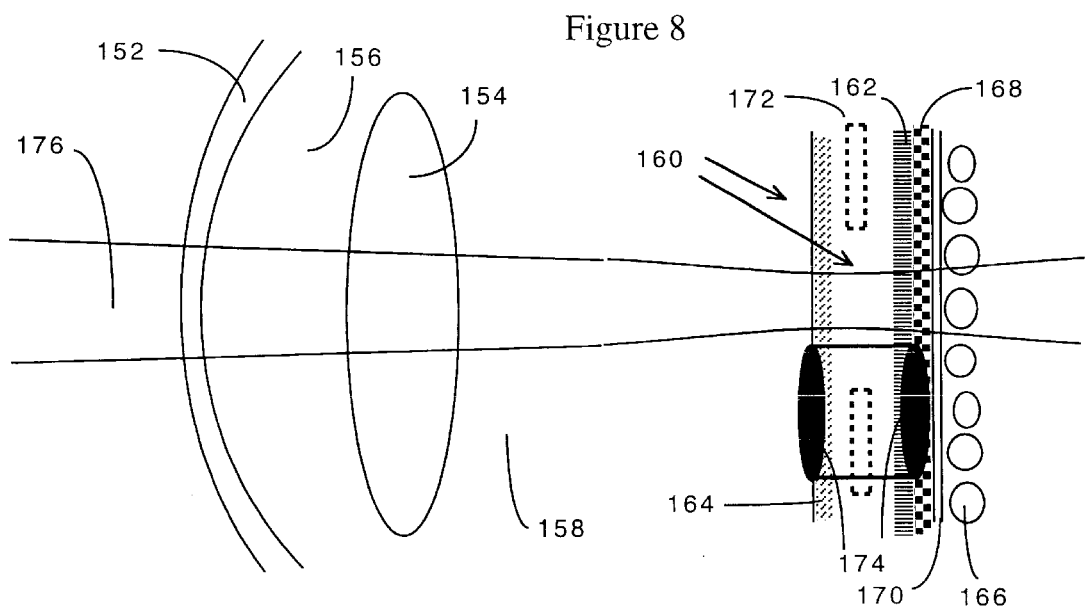
FIG. 8 illustrates a stationary ray tracing of the scanning lasers through the eye optics. The 1.0 mm beam focusses to a small spot of about 25.mu. in the retina, not to scale. The different retinal layers, virtual retinal conjugate aperture of about 100.mu. and backscatter rays of a non-scanning external laser source are indicated. The 75.mu. backscatter predominantly originates from the internal limiting membrane and pigment epithelium.
Figure 9:
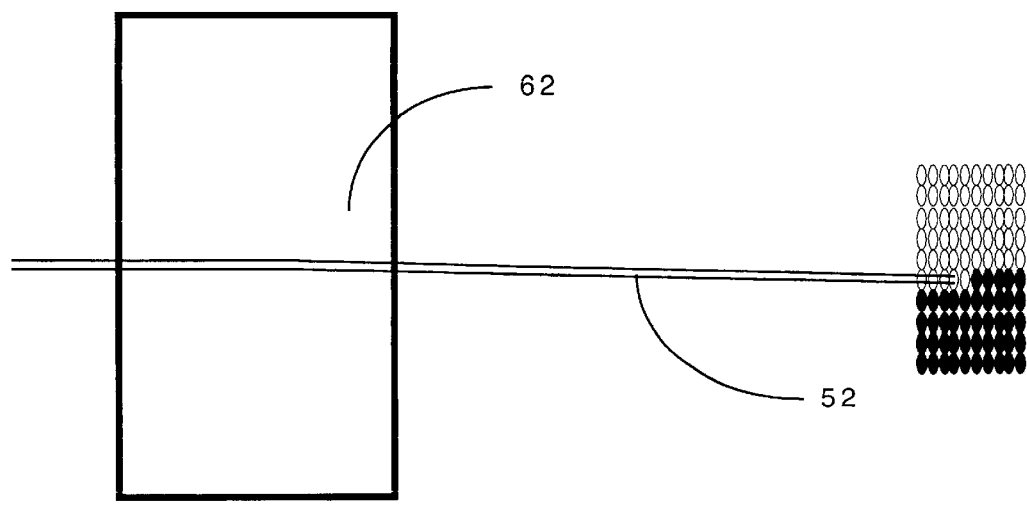
FIG. 9 illustrates the use of the two-dimensional acousto-optic modulator.
Figure 9:
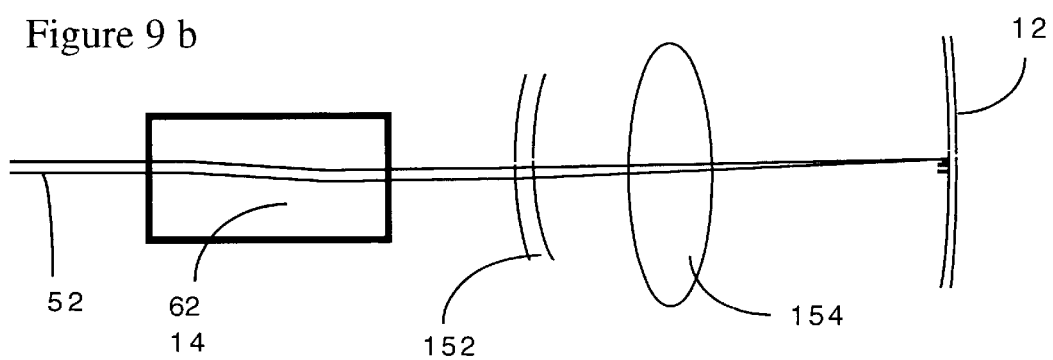
Figure 9:
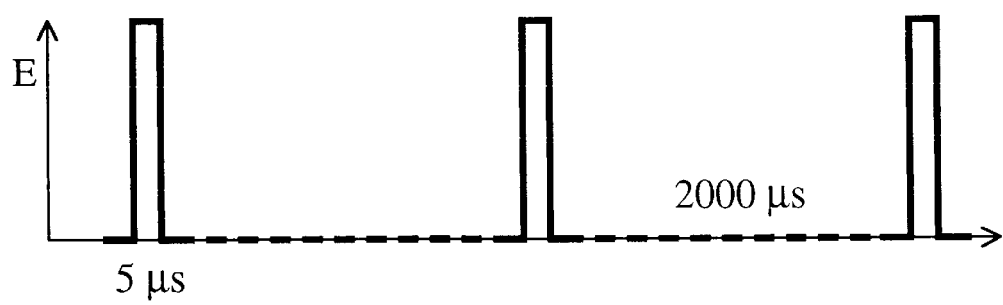

In FIG. 3b reflections at the anterior corneal surface are ray traced. Usually, the angle between incidence and reflection is small. As previously explained, strong direct perpendicular reflections 90 from the scanning lasers themselves are suppressed at the aperture 24, skewed angulated reflections 90 are mostly rejected because the confocal aperture 200, 202 is not looking at their virtual retinal location of origin. This mechanism of suppression does however not hold for the therapeutic lasers 52, 54 since their reflection 90 will be registered by the moving confocal aperture 200, 202. The moving of the aperture vis a vis a stationary therapeutic laser spot is illustrated in FIG. 8 and further explained below. This causes spurious reflections that can be confused with the real location of the therapeutic spot on the retina. To solve this problem, the 670 nm aiming beam 54 is polarized. The corneal interface index of refraction is approximately 1.33, therefore the intensity of reflection amounts to about 2%. The angle of reflection is usually much smaller than the Brewster angle of 53 degrees. In fact, up to 30 degrees of reflection angle, both s- and p-polarization components will be present. If the aiming beam 54 is polarized, this orientation will be primarily returned to the detector 28 where it can be intercepted with an orthogonal polarizer 48 e.g. Melles-Griot#03FPG001. An additional interference filter 48 e.g. Melles-Griot 03IFS014 can isolate 60 percent of the 670 nm light. It blocks the high intensity and non-polarized 532 nm. The optical media, e.g. nerve fibers, have a polarizing capacity that is incomplete, hence the mechanism of suppression will work. It is possible however to change the orientation of polarization according to the retinal location to maximize performance if necessary.

Figure 7:
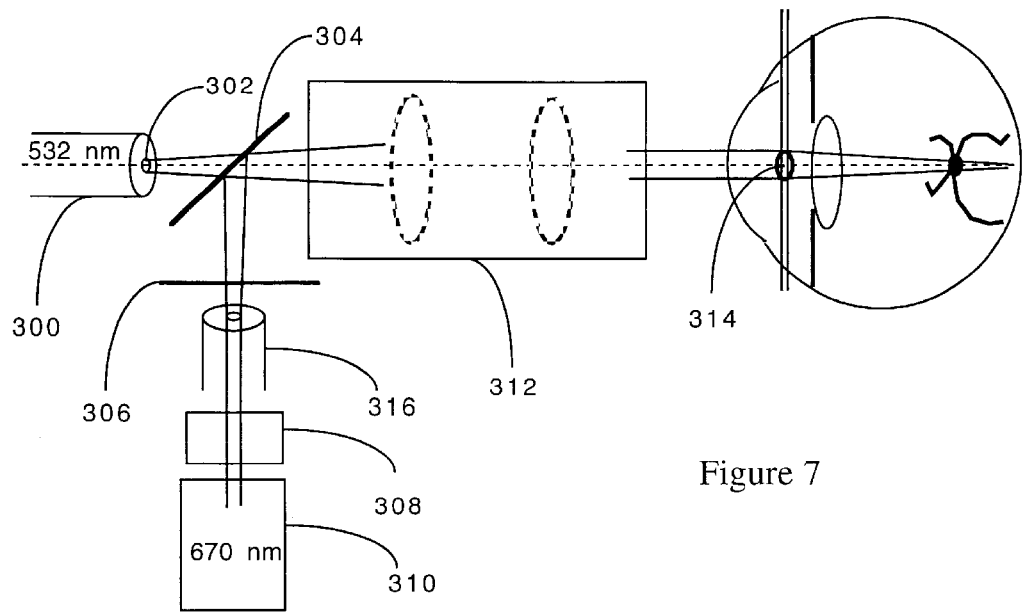
FIG. 7 is a schematic that illustrates the importance of a minimal fiber optic aperture and low N.A. to match the f/# of the receiving optics, i.e. the eye. Entrance pupil is limited to 2 mm. Back focal length of the eye is assumed to be 22.28 mm.

Focussing optics are illustrated in FIG. 7 and FIG. 8. In FIG. 7, the aperture of a multimodal cladded fiber optic with diameter of 75.mu. is in the object plane. Divergence of the mixed multimodal output beam of 532 nm is limited to a numerical aperture N.A. of about 0.05. A circular opening produces a clean edge and passes 90% of the output power. This beam is then merged with the aiming beam of 670 nm, properly polarized and having the same divergence characteristics, e.g. by sending this light through the same type of optical fiber. Further focussing optics including field lenses and the collimator-telescope 60 have been discussed. If the smallest spot size of 75.mu. on the retina is desired, then the magnification factor will be one and consequently the same N.A. or f/10 has to be used at the entrance pupil of the eye. The back focal length of the eye being 22.28 mm results in an entrance pupil of about 2 mm, which is a reasonable limit. Larger spot sizes will then require a smaller entrance diameter. From the discussion above it is clear that a fiber with minimal N.A. i.e. divergence, smallest diameter and minimal power loss is advantageous. The mode mixing within the fiber creates a reasonable flat profile at the exit aperture, thus avoiding the peaked central power of a Gaussian beam. Beamsplitters 50, 56 are specifically coated to reflect for the wavelength and polarization of the external lasers 52, 54, but are highly transparent for the wavelengths of the imaging scanning laser 38 of the scanning laser ophthalmoscope. Beamsplitter 03BTF011 from Melles-Griot reflects 70% of the 532 mm light, transmits 95% of the properly polarized 792 nm light, reflects 70% of the s-component of 670 nm, transmits 40% mixed polarization of 670 nm. An alternative beamsplitter, cold mirror Melles-Griot 03 MCS007 transmits 90% of 792 nm, reflects over 97% of 532 nm, and reflects 20% or transmits 80% of 670 nm light. The task of the beamsplitter 56 is to direct the external laser beams 52, 54 and various scanning diagnostic laser beams 38, 40 of the scanning laser ophthalmoscope towards the posterior pole of the eye 12. Some therapeutic laser light 52, 54 is however permitted to pass the beamsplitter 56 in order to reach a photodetector 28 after returning from the retina. The task of beamsplitter 50 is to direct the returning light from scanning lasers 38, 40 and external lasers 52, 54 to different detectors 28. E.g. Melles-Griot long wave pass filter 03 BDL001 separates the 532 and 670 nm from the 792 nm. The remaining transmitted therapeutic light 52, 54 after the beamsplitter 50 is absorbed by a filter 48 in front of one of the detectors, to avoid confusion with the descanned laser light 38 or 40 that is returning from the retina.

Figure 5:
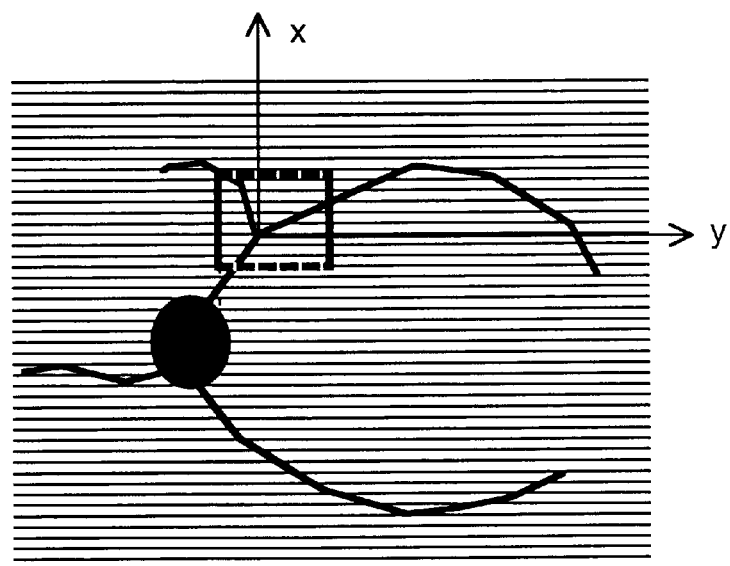
FIG. 5 details the contents of part of frame memory of an OFG card with video coming from a first detector. A search window within the video retinal image contains a gray scale pattern that is used to determine the coordinates of fiducial landmarks of the retina with a normalized gray-scale correlation algorithm.
Figure 6:
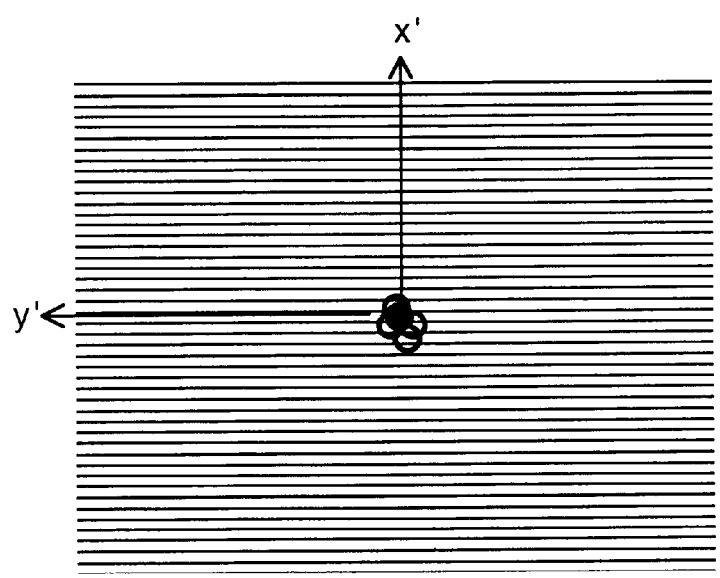
FIG. 6 details the contents of part of frame memory of an OFG card with video coming from a second synchronized detector. The coordinates of the location of the external beams can be determined with simple digital image processing techniques and indicated on the retinal image with the help of overlay graphics.

As mentioned before, both detectors 28 and circuitry 30 generate video that is genlocked to a common master timing signal derived from the spinning polygon. This property will be exploited in referencing the external laser beam location onto the retina. For this purpose one detector 28 is provided with a barrier filter 48 to eliminate all wavelengths of light returning from the retina except the external laser wavelength of 670 nm. Image processing is applied to determine the position of the light from the external laser beams in the video-signal. Because of the synchronization of the video generated from the detectors 28 within the overlay frame grabber graphic card(s) memory 32, a precise indication of the position of the external laser beams 52, 54 is possible using overlays 46 on the retinal image produced by the second detector 28. The overlay can be pseudo-colored and semi-transparent to imitate the look and feel of an aiming beam on the retina using the regular optical slitlamp. It is important to realize that this separation of laser beams at the detectors 28 is desired for multiple reasons. First, it is easier to see the progression of retinal coagulation in the absence of the treating light. Second, the high power of the external laser beams makes their precise localization on the retina impossible because of oversaturation of the video. Third, tracking algorithms as explained below cannot work efficiently in the presence of a retina that can move independently in a different direction when compared with the position on the retina of the external laser beam that can move in another direction. FIG. 5 and FIG. 6 summarize what is seen by the two synchronized detectors 28. In FIG. 5 only the scanning lasers 38, 40, and most often only the scanning IR laser 38 responsible for the retinal image, is contributing. The graphics however can be seen as overlays 46 as previously explained. Diverse retinal features can be used as fiducial landmarks, e.g. the branching pattern of vessels or pigmentary changes. In FIG. 6 only the external lasers 52, 54 will contribute to the image.

Conventional laser delivery systems can also be equipped with e.g. two monochrome CCD cameras that are attached to the slitlamp with the help of beamsplitters. One color CCD camera that registers the attenuated green light in one channel with the help of filters and the red fundus light on another channel can also be used. The spatial congruence is equivalent to the temporal alignment found in the SLO system. Overlay graphics can then be employed in a similar fashion and registration can also be performed.

Location, focussing, size, duration of application and intensity of the therapeutic laser beam can be stored, retrieved and used in other treatment sessions. It is also possible to plan laser applications at particular locations on forehand. Since the registration of the therapeutic laser beam location is happening in real-time, simultaneous retinal image registration using a technique outlined in the next chapter, will show whether the intended therapeutic laser beam location is still selected within the desired area on the retina. If the algorithm is fast enough real-time indication of the next location to be treated is possible. A map of treated locations is available to the surgeon. If a misalignment occurs, the TTL circuitry 66 will activate the shutter 62 and interrupt the therapeutic laser beam 52. This is very advantageous since such interruption is likely to occur much faster than human reaction would allow.

The external laser beams 52, 54 will generate a blurred image of the confocal aperture on the monitor 36. This can be understood by examining FIG. 8. In this FIG. 8, the scanning laser beam 176 is flying across the retina while transversing the dioptric media of the eye 152, 156, 154, 158. Further visualized are the virtual confocal aperture 172 situated at the waist of the scanning laser beam 176, and the different parts of the retina, 164, 170, 162, 168, 166. An external laser beam 52, 54 produces the stationary retinal spot 174. This retinal spot backscatters light, e.g. from the retinal pigment epithelium 168 and internal limiting membrane. If the confocal aperture is larger than the retinal spot, then a blurred image of the opening of the confocal aperture 172 will be generated on the monitor 36 through convolution of the external laser spot 174 with the confocal aperture. It is possible to enhance the resolution of the therapeutic spot by using a confocal aperture that is significantly smaller. One solution uses two adjacent confocal series of apertures 200 and 202, aperture 204 will be smaller but constructed of such material e.g. Kodak Wratten filter 89B that passes maximally the 792 nm light. This light then is filtered through the larger confocal aperture 206. The filter 204 is thin and can be placed at a variable distance from aperture 206. This feature can further reduce the small effects of chromatic longitudinal aberration. It should be noted that the aiming beam backscatter from the retina is only slightly polarized, the specular reflection from the anterior surface of the cornea is polarized, and the intensity has to be strong enough for appropriate detection. Hence the advantage of using a modulated external 670 nm diode laser that is pulsed at the retinal location of the therapeutic spot to prevent aliasing. The higher intensity is still safe and can be easily detected with a very small confocal aperture.

Alternative embodiments of the invention will use other wavelengths for treating the retina. The same optical principles however will hold. The characteristics of the optical filters have to be adjusted accordingly. Also, the coatings can be adjusted to accommodate an aiming beam of 635 nm instead of 670 nm. As such it is possible to use the built-in 635 nm of the Iris 532 nm laser by separating, polarizing and recombining the beams. Minimal losses of 532 nm will occur. For microperimetric purposes, increased 633 nm transmission would increase the visibility of the fixation light for the subject.

IV. The Overlay Frame Grabber and Image Processing Techniques

Figure 4:
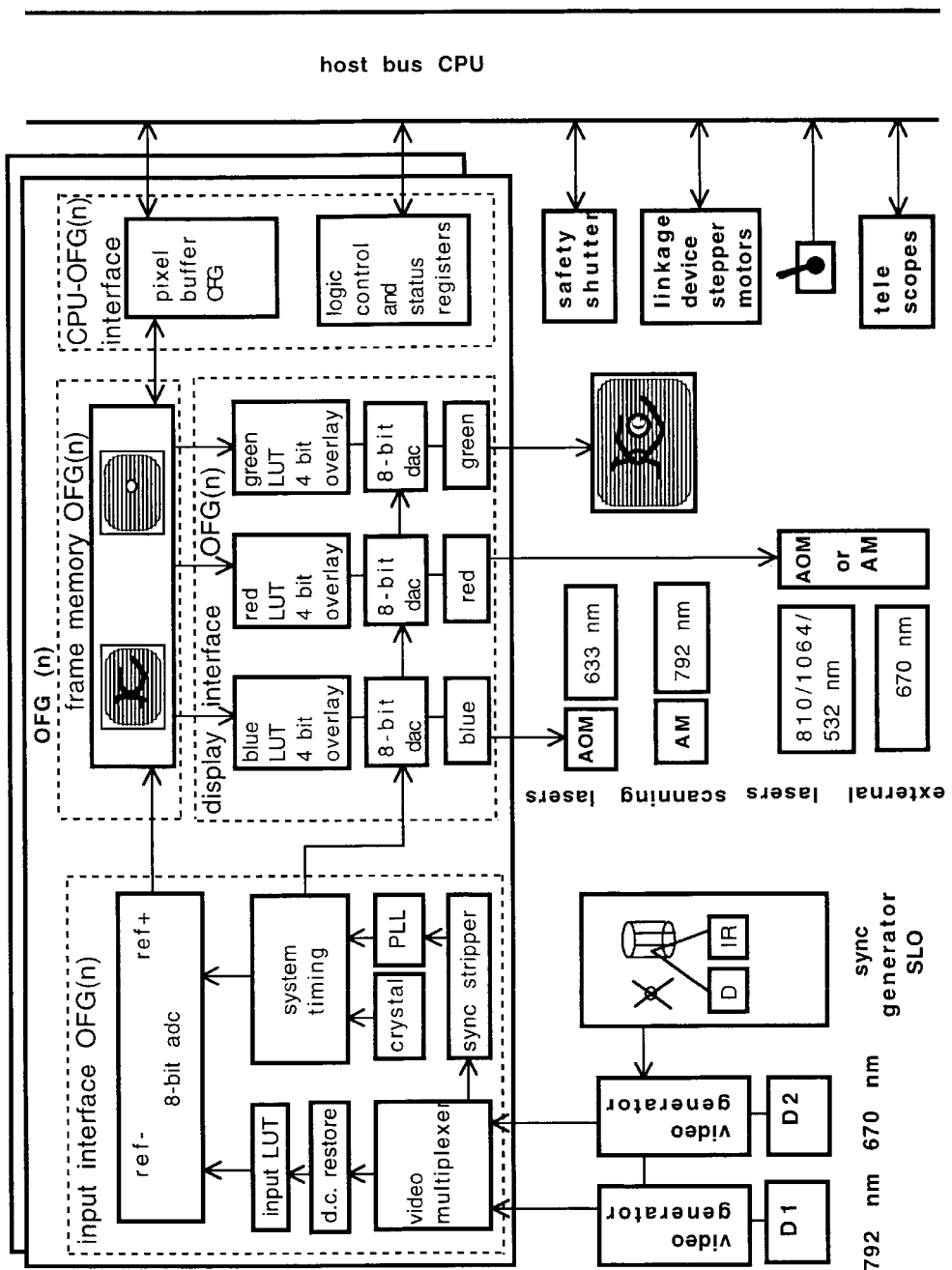
FIG. 4 shows a block diagram of an overlay frame grabber card capable of advanced image processing. The one or more overlay frame grabber graphic cards have an input interface, frame memory, display interface and CPU interface. Besides the OFG cards, the host bus accommodates a I/O for interaction with several components of the therapeutic laser assembly and opto-mechanical linkage device. Essential electronic pathways include: (1) Synchronized video-in pathway from SLO detectors. (2) Video-out pathway to monitor and laser modulators. (3) System timing generator with further genlocking of the other components including A/D converters and D/A converters of the different boards.

Indispensable for processing the video that is generated by the scanning laser ophthalmoscope laser sources 38, 40 and external laser source 52, 54, and for the production of graphics that will be projected onto the retina, is an overlay frame grabber graphics card 32, schematized in FIG. 4. A good example is the Imaging Technology OFG card in a 90 Mhz Pentium PC. This overlay frame grabber graphics card 32 can accept four different video input sources, and digitizes the incoming video signals to eight bits of accuracy, at a rate of 60 fields per second (RS-170). On board frame memory can store two 512 by 480 pixel video frames or one larger 512 by 512 pixel video frame. Two or more overlay frame grabber cards 32, which are I/O mapped, can reside in one computer 34. This versatility is advantageous when combining the signals from a multidetector scanning laser ophthalmoscope, e.g. in simultaneous recording of the aiming laser beam location on the retina with one detector 28 and the retinal image itself with another detector 28.

The analog-to-digital converter of the frame grabber card 32 has programmable negative and positive reference values for calibrating the white and black video signal levels. A look-up table (LUT) controls the input video and can be used for preprocessing contrast and intensity. This feature is particularly useful in facilitating normalized gray scale correlation, a digital image processing technique further explained. It can also be used to separate the aiming beam pixels from noise pixels.

An additional four bits per pixel control the instantaneous switching between 16 different output look-up tables for each pixel. Three independent output channels are provided for each imaging board. The output channels generate RS-170 video adapted for pseudo-color display. Output LUT programming is a well known solution for creating nondestructive graphic overlays. Non-destructive graphic overlays 46, drawn over the incoming video signal, generate the graphics visible in the laser raster of the scanning laser ophthalmoscope and indicate the position on the retina of the aiming laser beam. The overlay 46 can be semi-transparent to imitate the look and feel of a real aiming beam when using the slitlamp coagulator. In FIG. 4, the green output video channel sends the retinal image to the monitor 36, overlaid with graphics indicating the aiming therapeutic laser beam location. The blue output channel of the original video signal is transformed into pure graphics. It controls the acousto-optic modulator 44 and defines what is visible to the observer in the scanning laser ophthalmoscope. This is typically a reference fixation target or test stimulus. The remaining red output channel can be used for different purposes. One option is the control of the acousto-optic modulator to create a pulsating external laser beam 54. An important feature of the overlay frame A grabber card is the capability to synchronize frame grabber memory D/A, A/D converters, to the external video source using a phase-locked loop. This is important since the timing signals provided by the high speed rotating polygon are slightly irregular. Digital image processing techniques are used for the tracking of a fiducial landmark in the retinal image as in FIG. 5. The overlay frame grabber card 32, or an external faster card connected to the computer 34, can perform this task using for example a technique called two-dimensional normalized gray-scale correlation. Such software is provided by Imaging Technology, Inc, Bedford, Mass. In two-dimensional normalized gray-scale correlation a characteristic search pattern, such as the branching of retinal vessels or the actual area of treatment is located within the video images provided by a detector 28 of the scanning laser ophthalmoscope. Sub-pixel accuracy is possible and sometimes necessary for the determination of small displacements in the presence of wavefront aberrations. Locating the aiming laser beam on the retina, as in FIG. 6, and modulating the aiming beam in an anti-aliased fashion, is realized using a combination of foregoing techniques. The aiming beam location is already approximately known by the computer if it takes into account the mechanical displacement of the joystick-manipulator 78. To facilitate the localization of the external aiming laser beam, the reference image in frame memory contains no retinal details as in FIG. 5; for facilitating the tracking of a fiducial landmark on the retina, the fundus image in frame memory is devoid of the therapeutic laser light, as in FIG. 6.

Although the description of the invention contains many specifications, these should not be construed as limiting the scope of the invention but as merely providing an illustration of the presently preferred embodiment of this invention. For example, the two-dimensional acousto-optic deflector can be replaced by a combination of two galvanometer driven mirrors.

Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A scanning laser ophthalmoscope capable of placing therapeutic laser spot applications onto a retinal location under continuous observation of said retinal location with said scanning laser ophthalmoscope, comprising the elements of:

A. said scanning laser ophthalmoscope, having at least one scanning laser source producing sufficient power output to obtain a raster video image of the retina, said scanning laser ophthalmoscope having optoelectronic means for scanning said laser sources through a single pivot point, said scanning laser ophthalmoscope also having mechanical means to adjust the position of said pivot point to minimize the effect of optical aberrations on the retinal image, said scanning laser ophthalmoscope further containing optical means for focussing said laser sources on the desired level inside the eye;

B. at least one external non-scanning therapeutic laser source, capable of retinal photocoagulation, combined with focussing means to adjust the position of the beam waist inside the eye;

C. a transmission system comprising a beamsplitter and optomechanical linkage device, said beamsplitter mostly but not completely reflecting said external non-scanning therapeutic laser source towards the eye optics so that some of the returning light from the retina will be transmitted by said beamsplitter into said scanning laser ophthalmoscope, said beamsplitter further transmitting optimally said scanning laser sources in both directions, and said optomechanical linkage device having sufficient adjustable support elements to create a second pivot point for said therapeutic laser source, in addition to additional support elements to move said second pivot point relative to said pivot point of said scanning laser sources;

D. first photodetecting means, synchronized with a second photodetecting means, for receiving selectively the backscattered light from said scanning laser sources after said backscattered light has passed through a confocal aperture, using optical elements comprising a beamsplitter and filters that are appropriately coated, thus creating a videosignal that contains mostly the image of the retina, devoid of light from said external non-scanning laser source;

E. said second photodetecting means for receiving selectively the backscattered light of said external non-scanning therapeutic laser beams after said backscattered light has passed through a confocal aperture, in association with optical elements comprising a beamsplitter and filters that are appropriately coated to eliminate as much as possible the backscattered light produced by the scanning laser beams, thus creating a videosignal that contains the information concerning the location of said external non-scanning therapeutic laser beams on the retina;

F. a computer capable of digital image processing including the generation of overlay graphics, said computer receiving the video signals from said first and second photodetecting means purposes, said computer capable of indicating with overlays the position of said external laser beam on the retinal image produced by first photodetecting means;

whereby it becomes possible to continuously visualize said retinal location on a monitor, position and focus said therapeutic laser onto said retinal location with minimal aberrations, activate said therapeutic laser source for variable amounts of time while monitoring the position of said retinal location and observing the progression of the therapeutic laser application.

2. The scanning laser ophthalmoscope optimized for retinal photocoagulation according to claim 1, wherein said opto-mechanical linkage device includes a succession of mirror interfaces and structural support means joined together so that enough degrees of freedom exist to move said therapeutic laser beam freely along a virtual surface that is curved.

3. The scanning laser ophthalmoscope according to claim 1 wherein said external therapeutic laser source is replaced with a diagnostic external laser source for the purpose of reconstructing the wavefront aberrations of the eye.

4. The scanning laser ophthalmoscope according to claim 1, further comprising the improvement of having means for interrupting said therapeutic beam including electronic circuit connecting attenuating means for said therapeutic beam and said computer with said overlay frame grabber card, said electronic circuit triggering said attenuating means upon sufficient displacement of said retinal location in frame memory of said overlay frame grabber card as determined by digital processing of grabbed said video images; whereby it becomes possible to attenuate said therapeutic laser beam in case of misalignment, faster than human reaction time would allow.

5. The scanning laser ophthalmoscope of claim 1 further having the improvement of a modulating means for said external therapeutic laser source, said modulating means under electronic control in order to pulse said external therapeutic laser source.

6. The scanning laser ophthalmoscope of claim 5 where modulating means is a two-dimensional acousto-optic deflector, whereby the therapeutic spot can be made of a multitude of Gaussian beam focused elementary spots guided by the focusing of said laser source of said scanning laser ophthalmoscope.

* * * * *